June 4, 1968 W. M. TRUMBULL Plant Pat. 2,816
APPLE TREE
Filed Feb. 8, 1967
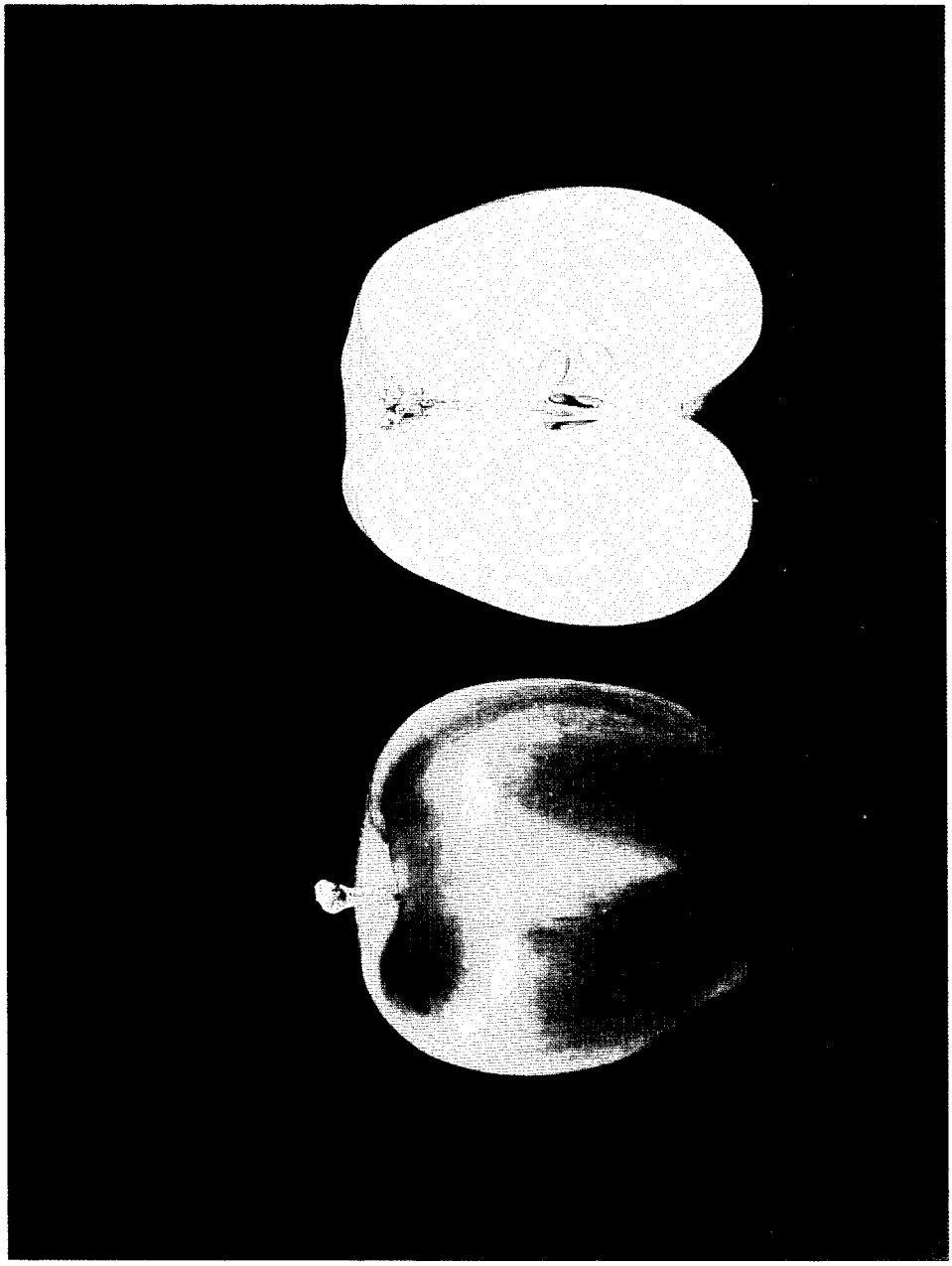
INVENTOR,
WAYNE M. TRUMBULL
BY
Christensen, Sanborn & Matthews
ATTORNEYS United States Patent Office Plant Pat. 2,816
Patented June 4, 1968

2,816
APPLE TREE

Wayne M. Trumbull, Milton-Freewater, Oreg., assignor to Van Well Nursery, Inc., Wenatchee, Wash.

Filed Feb. 8, 1967, Ser. No. 614,757
1 Claim. (Cl. Plt.—35)

ABSTRACT OF THE DISCLOSURE

The subject apple tree comprises a new Red Delicious variety originating as a sport limb on a Brauns variety tree, Plant Patent No. 1,411. In contrast with its parent the new variety is of the spur type and its fruit colors approximately two weeks earlier than that of its parent and becomes a darker and more intensely red with a heavier underlying striped formation.

*Description*

The present new and distinct variety of apple tree was originally discovered as a sport limb mutation growing on a Brauns variety Delicious apple tree (Plant Patent No. 1,411) in my cultivated apple orchard in Milton-Freewater, Oreg. It has been reproduced to the third generation by budding and grafting in the aforementioned orchard; also in the Van Well Nursery orchard in Wenatchee, Wash., and has thereby been proven to be a new and distinct variety.

For purposes of comparison the second and third generation trees have been grown alongside trees of the aforesaid Brauns Delicious variety, Cooper Delicious variety (Plant Patent No. 2,606), Wellspur Delicious variety (unpatented), Bisbee Delicious variety (Plant Patent No. 1,565) and Woods Delicious variety (Plant Patent No. 1,930).

This new variety has characteristics nearest resembling those of its parent, Brauns, except its fruit starts coloring from ten to fourteen days earlier than that of its parent and its growth resembles the spur-type growth of Wellspur and Bisbee, whereas the growth of its parent resembles that of the Standard Red Delicious tree (i.e. Starking).

The predominant distinguishing characteristic of the new variety compared with Bisbee, Wellspur, Ryan (unpatent), Houser (unpatented) and other spur-type Red Delicious trees (excepting Cooper and Woods) is that apples of the new variety start coloring with a striped formation and when a finished color is attained the striped formation is still clearly visible as lighter areas underlying the deep and intense overall red color. It differs principally from both Cooper and Woods in that its fruit starts coloring about five days ahead of Cooper and fifteen to twenty days ahead of Woods, and becomes darker red, with a heavier and more predominant stripe formation, than either Cooper or Woods.

The accompanying drawing comprises a color photograph of the fruit of the new variety shown both in axial cross-section and in side view.

Fruit of the new variety is generally uniform in size averaging approximately three inches in axial diameter and 3 1/16 inches in transverse diameter. Cavity is symmetrical, approximately ½ inch deep by 1 3/16 inches broad. Calyx is closed. Skin is smooth, medium thick, similar to Brauns. Color is approximately Carmine, Plate 1, Ridgway-Color Standards and Nomenclature, with stripe coloration, clearly showing when finished color is reached, between Oxblood Red, Plate 1, and Bordeaux, Plate 12, (Ridgway). Stem is medium length, brown, stout. Seeds are similar to those of Brauns.

Having thus described this new and distinct variety of apple tree I claim:

1. The new and distinct variety of apple tree characterized particularly by the earlier coloring of its fruit and by its spur-type growth, contrasting it with its parent Brauns, and by its earlier fruit coloration and more intense and deeply red coloration, with more prominently visible underlying stripe formation distinguishing it from other spur-type Red Delicious varieties, substantially as shown and described.

No references cited.

ROBERT E. BAGWILL, *Primary Examiner.*